US012099151B2

(12) United States Patent
Hosemann

(10) Patent No.: US 12,099,151 B2
(45) Date of Patent: Sep. 24, 2024

(54) EVALUATION UNIT FOR AN X-RAY DETECTOR, X-RAY DETECTOR, MEDICAL IMAGING DEVICE AND METHOD FOR OPERATING AN X-RAY DETECTOR

(71) Applicant: Siemens Healthcare GmbH, Erlangen (DE)

(72) Inventor: Michael Hosemann, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 102 days.

(21) Appl. No.: 17/409,973

(22) Filed: Aug. 24, 2021

(65) Prior Publication Data

US 2022/0066054 A1    Mar. 3, 2022

(30) Foreign Application Priority Data

Aug. 31, 2020 (DE) ............ 10 2020 210 957.5

(51) Int. Cl.
*G01T 1/17* (2006.01)
*A61B 6/03* (2006.01)
*H04N 5/32* (2023.01)

(52) U.S. Cl.
CPC ............ *G01T 1/17* (2013.01); *A61B 6/032* (2013.01); *H04N 5/32* (2013.01)

(58) Field of Classification Search
CPC ............ A61B 6/032; G01T 1/17; H04N 5/32
See application file for complete search history.

(56) References Cited

U.S. PATENT DOCUMENTS

| 4,593,198 A | 6/1986 | Pang et al. |
| 4,718,057 A * | 1/1988 | Venkitakrishnan ............ H04Q 11/0428 370/524 |
| 5,402,460 A * | 3/1995 | Johnson ............... G01N 23/046 378/10 |
| 5,751,000 A * | 5/1998 | McCroskey .......... G01T 1/1648 250/363.02 |
| 7,995,113 B2 * | 8/2011 | Karim ................... H04N 25/00 348/308 |
| 8,120,683 B1 * | 2/2012 | Tumer .............. H01L 27/14634 348/295 |
| 8,772,730 B2 | 7/2014 | Han et al. |

(Continued)

FOREIGN PATENT DOCUMENTS

| CN | 101889869 A | 11/2010 |
| CN | 105581804 A | 5/2016 |

(Continued)

*Primary Examiner* — Blake C Riddick
(74) *Attorney, Agent, or Firm* — Harness, Dickey & Pierce, P.L.C.

(57) ABSTRACT

An evaluation circuit for an x-ray detector for signaling coupling to a converter, designed to convert incident x-radiation into electrical signals. In at least one embodiment, the evaluation circuit includes a multiplicity of pixel-electronics modules. A respective pixel-electronics module is designed to process electrical signals fed into the respective pixel-electronics module from the converter, order to produce a respective digital pixel-measurement signal. Further, each of the respective pixel-electronics modules has at least one respective settable digital signal-processor, designed to adapt a respective processed digital pixel-measurement signal in a respective pixel-electronics module.

28 Claims, 6 Drawing Sheets

(56) References Cited

U.S. PATENT DOCUMENTS

| | | | |
|---|---|---|---|
| 2002/0114426 A1* | 8/2002 | Polkus | A61B 6/4233 378/207 |
| 2003/0142787 A1* | 7/2003 | Jabri | A61B 6/482 378/98.12 |
| 2003/0181808 A1* | 9/2003 | McKinnon | A61B 6/00 600/411 |
| 2005/0084176 A1* | 4/2005 | Talapov | A61B 5/444 382/128 |
| 2007/0023669 A1 | 2/2007 | Hefetz et al. | |
| 2007/0202836 A1* | 8/2007 | Zaman | G06F 1/3203 455/343.2 |
| 2007/0273697 A1* | 11/2007 | Zaman | A61B 6/465 345/501 |
| 2007/0274439 A1* | 11/2007 | Boucly | H04N 5/32 378/38 |
| 2008/0298541 A1* | 12/2008 | Mattson | A61B 6/585 378/19 |
| 2010/0296627 A1 | 11/2010 | Inoue et al. | |
| 2011/0036988 A1* | 2/2011 | Campbell | G01T 1/247 250/370.07 |
| 2011/0211670 A1* | 9/2011 | Dugas | G01N 23/223 378/45 |
| 2012/0223241 A1 | 9/2012 | Kim et al. | |
| 2012/0228486 A1 | 9/2012 | Herrmann et al. | |
| 2012/0236986 A1* | 9/2012 | Schroter | G01T 1/171 250/371 |
| 2013/0105701 A1* | 5/2013 | Han | G01T 1/366 250/336.1 |
| 2013/0214144 A1* | 8/2013 | Hannemann | G01T 1/17 250/252.1 |
| 2013/0343522 A1* | 12/2013 | Yoon | H04N 5/32 250/394 |
| 2014/0016748 A1* | 1/2014 | Spahn | G01T 1/245 250/370.08 |
| 2014/0044232 A1* | 2/2014 | Liu | H04N 5/32 378/62 |
| 2015/0381183 A1* | 12/2015 | Schultz | H03M 1/001 377/118 |
| 2016/0131771 A1 | 5/2016 | Kappler | |
| 2016/0306056 A1 | 10/2016 | Sun et al. | |
| 2017/0090048 A1* | 3/2017 | Groepl | G01T 1/247 |
| 2017/0097810 A1* | 4/2017 | Manohararajah | G06F 7/5443 |
| 2017/0192112 A1* | 7/2017 | Sandvik | G01T 1/249 |
| 2017/0254907 A1* | 9/2017 | Ergler | G01T 1/18 |
| 2017/0273640 A1* | 9/2017 | Danielsson | H04N 5/32 |
| 2017/0285186 A1 | 10/2017 | Roessl et al. | |
| 2017/0322619 A1* | 11/2017 | Eismann | A61B 6/42 |
| 2017/0354389 A1* | 12/2017 | Eichenseer | G01T 1/00 |
| 2018/0020177 A1 | 1/2018 | Geese et al. | |
| 2018/0028141 A1* | 2/2018 | Kuwabara | A61B 6/56 |
| 2018/0081071 A1 | 3/2018 | Cao et al. | |
| 2018/0146535 A1* | 5/2018 | Goederer | G01T 1/17 |
| 2018/0350075 A1* | 12/2018 | Grimmer | G06T 7/40 |
| 2019/0172231 A1* | 6/2019 | Polster | A61B 6/5258 |
| 2020/0132864 A1* | 4/2020 | Shimizukawa | H04N 25/75 |
| 2022/0166948 A1* | 5/2022 | Kelly | H04N 23/56 |

FOREIGN PATENT DOCUMENTS

| | | |
|---|---|---|
| CN | 105899137 A | 8/2016 |
| CN | 106030345 A | 10/2016 |
| CN | 106154305 A | 11/2016 |
| CN | 107167648 A | 9/2017 |
| CN | 107615095 A | 1/2018 |
| CN | 107623826 A | 1/2018 |
| WO | WO 2016/197338 A1 | 12/2016 |

* cited by examiner

EVALUATION UNIT FOR AN X-RAY DETECTOR, X-RAY DETECTOR, MEDICAL IMAGING DEVICE AND METHOD FOR OPERATING AN X-RAY DETECTOR

PRIORITY STATEMENT

The present application hereby claims priority under 35 U.S.C. § 119 to German patent application number DE102020210957.5 filed Aug. 31, 2020, the entire contents of which are hereby incorporated herein by reference.

FIELD

Example embodiments of the invention generally relate to an evaluation unit for an x-ray detector, the evaluation unit comprising a multiplicity of pixel-electronics modules, wherein each pixel-electronics module has a settable digital signal-processing unit which is designed to adapt a processed digital pixel-measurement signal in a respective pixel-electronics module. Example embodiments of the invention further generally relate to an x-ray detector comprising an evaluation unit, a medical imaging device comprising an x-ray detector, and a method for operating an x-ray detector.

BACKGROUND

X-ray detectors are used in many imaging applications. For example, x-ray detectors are used in computed tomography systems for medical imaging in order to generate a tomographic x-ray image of an examination region of a patient.

In x-ray imaging, e.g. in computed tomography, angiography or radiography, it is possible to use counting x-ray detector devices with direct conversion or integrating x-ray detector devices with indirect conversion.

In direct-conversion x-ray detector devices, the x-radiation or the photons can be converted into electrical pulses by way of a suitable converter material. Possible converter materials include CdTe, CZT, CdZnTeSe, CdTeSe, CdMnTe, InP, $T_1Br_2$, $HgI_2$ or GaAs, for example. The electrical pulses can be evaluated by electronic circuits of an evaluation unit, e.g. in the form of an integrated circuit (application-specific integrated circuit, ASIC). In the case of counting x-ray detector devices, the incident x-radiation can be measured by counting the electrical pulses that are triggered by the absorption of x-ray photons in the converter material. The magnitude of the electrical pulse is moreover generally proportional to the energy of the absorbed x-ray photon. Spectral information can therefore be derived by comparing the magnitude of the electrical pulse with a threshold value.

In indirect-conversion x-ray detector devices, the x-radiation or the photons can be converted into light by way of a suitable converter material and into electrical pulses via optically coupled photodiodes. Scintillators such as GOS ($Gd_2O_2S$), CsJ, YGO or LuTAG, for example, are often used as a converter material. The electrical signals that have been generated are then postprocessed by an evaluation unit comprising electronic circuits. Scintillators are used in particular in medical x-ray imaging in the energy range up to 1 MeV.

In this case, the electronic circuits of an x-ray detector device can be used for the purpose of e.g. signal amplification, digitization (A/D converter, analog-to-digital converter) or other postprocessing of the electrical signals before forwarding to a readout electronics module, from which the processed data can be forwarded to a computing unit. The computing unit can then be designed to generate an x-ray image data record based upon the processed signals that have been forwarded.

In this case, x-ray detector devices and in particular the converter units concerned, whether direct-conversion or indirect-conversion, can suffer from time-dependent, radiation-dependent and/or temperature-dependent drift effects which can impair the image quality of an image data record that is recorded by an x-ray detector device. Such drift effects can be reduced by way of costly materials handling and stabilization of the operating conditions. However, the possibility of correcting the digital measurement data that is output by the x-ray detector is also desirable in order to achieve further improvements in the measurement data records that are generated by an x-ray detector, such that high-quality imaging can be guaranteed.

SUMMARY

At least one embodiment of the invention provides a device/method by which pixel-measurement signals can be adapted in an efficient manner.

Further advantageous and in part per se inventive embodiment variants and developments of the invention are set forth in the claims and in the following description.

At least one embodiment of the invention relates to an evaluation device for an x-ray detector for the signaling coupling to a converter which is designed to convert incident x-radiation into electrical signals. The evaluation device comprises a multiplicity of pixel-electronics modules, wherein a respective pixel-electronics module of the multiplicity of pixel-electronics modules is designed to process the electrical signals which are fed into a pixel-electronics module from the converter, and to produce a digital pixel-measurement signal. Each of the multiplicity of pixel-electronics modules also comprises at least one settable digital signal-processor, which is designed to adapt a processed digital pixel-measurement signal in a respective pixel-electronics module of the multiplicity of pixel-electronics modules.

Furthermore, at least one embodiment of the invention relates to an x-ray detector comprising an evaluation unit as per at least one embodiment of the invention and a converter unit, wherein each pixel-electronics module of the multiplicity of pixel-electronics modules is coupled in an electrically conductive manner to the converter unit for the purpose of signaling, in order to feed electrical signals into the pixel-electronics module.

Furthermore, at least one embodiment of the invention relates to a medical imaging device comprising at least an x-ray detector of at least one embodiment with an evaluation unit, and an x-ray source which is situated opposite the x-ray detector and is designed to expose the x-ray detector to x-radiation.

Furthermore, at least one embodiment of the invention relates to an evaluation circuit for an x-ray detector for signaling coupling to a converter, designed to convert incident x-radiation into electrical signals, the evaluation circuit comprising:

a multiplicity of pixel-electronics modules, a respective pixel-electronics module of the multiplicity of pixel-electronics modules being designed to process the electrical signals, fed into the respective pixel-electronics module from the converter, to produce a respective processed digital pixel-measurement signal, and each respective pixel-electronics module of the multiplicity of pixel-electronics modules including
at least one settable digital signal-processor designed to adapt a respective processed digital pixel-measurement signal in a respective pixel-electronics module.

Furthermore, at least one embodiment of the invention relates to an x-ray detector, comprising:
the evaluation circuit of an embodiment; and
a converter, wherein each respective pixel-electronics module of the multiplicity of pixel-electronics modules is coupled in an electrically conductive manner to the converter to feed electrical signals into the respective pixel-electronics module.

Furthermore, at least one embodiment of the invention relates to a medical imaging device, comprising:
at least one of the x-ray detector of an embodiment; and
an x-ray source, situated opposite the at least one x-ray detector, designed to expose the x-ray detector to x-radiation.

Furthermore, at least one embodiment of the invention relates to a method for operating an x-ray detector, comprising:
exposing a converter of the x-ray detector to x-radiation via an x-ray source, to generate electrical signals in the converter, the electrical signals being fed into a multiplicity of pixel-electronics modules of an evaluation circuit of the x-ray detector via the electrically conductive coupling;
processing the electrical signals, via respective pixel-electronics modules of the multiplicity of pixel-electronics modules, to form respective digital pixel-measurement signals; and
adapting at least one respective digital pixel-measurement signal of the digital pixel-measurement signals, in a respective pixel-electronics module, via a settable digital signal-processor of the respective pixel-electronics module.

All of the embodiment variants described above in connection with the inventive evaluation unit can also be realized in the medical imaging device comprising an x-ray detector with an evaluation unit according to at least one embodiment of the invention. The description in relation to the evaluation unit and the advantages described above can also be transferred to the inventive medical imaging device correspondingly.

At least one embodiment of the invention further relates to a method for operating an x-ray detector according to one of the embodiments described above. The method comprises the steps of the exposure, the processing and the adaptation.

BRIEF DESCRIPTION OF THE DRAWINGS

The invention is explained below with reference to example embodiment variants and with reference to the appended figures. The illustrations in the figures are schematic, greatly simplified and not necessarily in proportion. The same reference signs are used for identical features in different figures.

DETAILED DESCRIPTION OF THE EXAMPLE EMBODIMENTS

Figure 1:
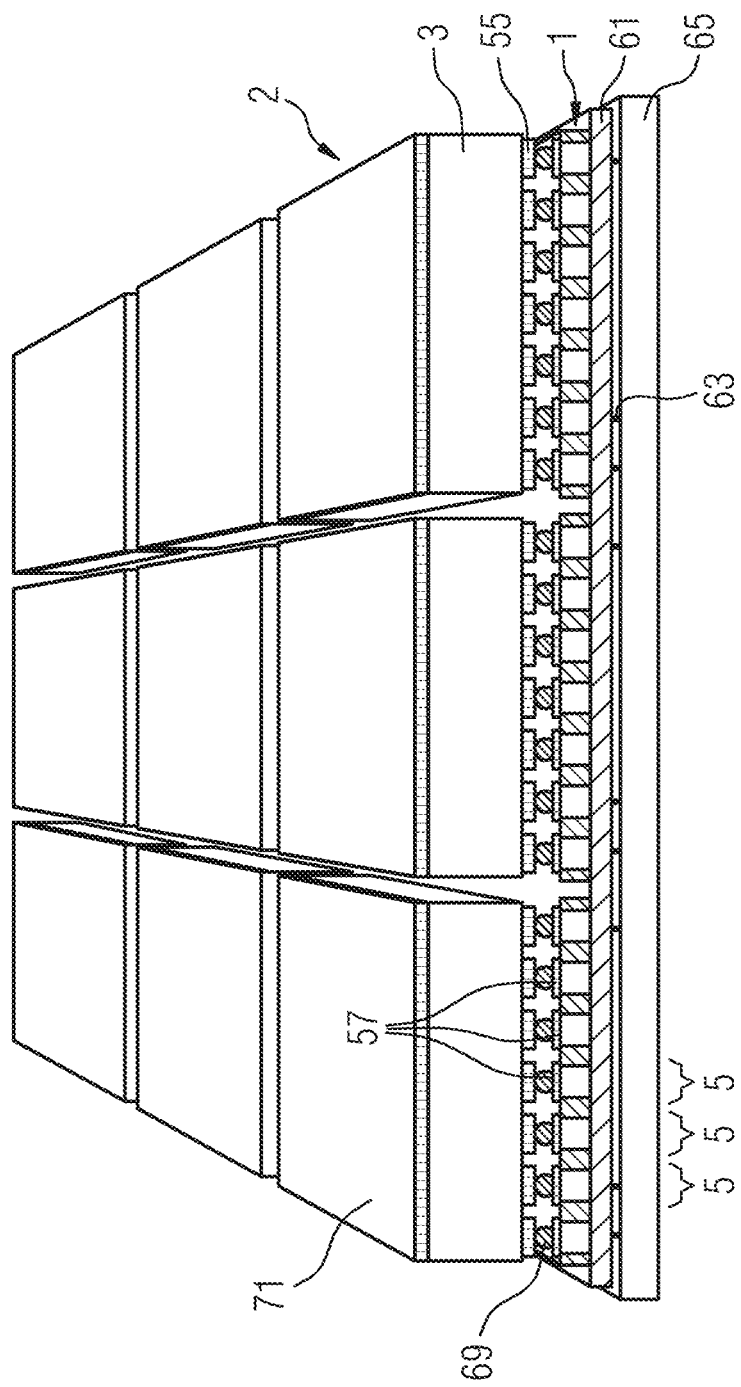
FIG. 1 shows a schematic illustration of a design variant of an example x-ray detector with an evaluation unit.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element (s) or feature (s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to an evaluation circuit/device/unit for an x-ray detector for the signaling coupling to a converter which is designed to convert incident x-radiation into electrical signals. The evaluation unit comprises a multiplicity of pixel-electronics modules, wherein a respective pixel-electronics module of the multiplicity of pixel-electronics modules is designed to process the electrical signals which are fed into a pixel-electronics module from the converter or converting unit, and to produce a digital pixel-measurement signal. Each of the multiplicity of pixel-electronics modules also comprises at least one settable digital signal-processor, which is designed to adapt a processed digital pixel-measurement signal in a respective pixel-electronics module of the multiplicity of pixel-electronics modules.

The evaluation unit can be designed as an integrated circuit. In particular, the evaluation unit can be designed as an application-specific integrated circuit (ASIC). The implementation adapting for the pixel-measurement signals in the evaluation unit itself, in particular in an ASIC, can contribute to particularly efficient adaptation.

In this case, a converter that is coupled to the evaluation unit can be designed as a direct-conversion converter comprising a direct-conversion converter material. The converter can however also be designed as an indirect-conversion converter. In this case, the converter can comprise e.g. a scintillator material and a number of photodiodes coupled thereto.

The evaluation unit can be coupled to the converter via electrically conductive connections. For example, each of the multiplicity of pixel-electronics modules of the evaluation unit can have a signal input, or a plurality of signal inputs, which is designed to feed electrical signals from the converter into a pixel-electronics module when the evaluation unit is coupled to the converter for the purpose of signaling via electrically conductive connections.

A respective pixel-electronics module of the multiplicity of pixel-electronics modules of the evaluation unit can comprise analog and digital circuit elements. An inventive pixel-electronics module of the multiplicity of pixel-electronics modules can be designed at least to receive an electrical signal from a converter via at least one signal input when the signal input is coupled to a converter, to digitize an electrical signal that has been fed in, e.g. via an A/D converter (analog-to-digital converter), such that, based upon the processing of a signal that has been fed in from a coupled converter, a digital pixel-measurement signal can be provided in a pixel-electronics module, and to adapt the digital pixel-measurement signal via the inventive signal-processing unit. A pixel-electronics module can also comprise a signal output at which, following adaptation by the digital signal-processing unit in the pixel-electronics module, an adapted digital pixel-measurement signal can be output.

A respective pixel-electronics module can have only one signal input that can be directly coupled to the converter.

However, designs are also possible wherein provision is made, in a pixel-electronics module of the multiplicity of pixel-electronics modules, for combining signals from a plurality of signal inputs that can be coupled to a converter unit, and wherein a pixel-electronics module, based upon the combined signals from a plurality of signal inputs, provides a digital pixel-measurement signal which can be adapted via the digital signal-processing unit of the pixel-electronics module. In this case, the combination can be performed before or after digitization of the signals that have been fed into the pixel-electronics module by the signal inputs.

In addition to digitization, a pixel-electronics module can be designed to amplify or shape a signal that is fed in from a converter unit. A pixel-electronics module can also comprise at least one comparator which is designed to compare a signal that is fed in via a signal input, and possibly amplified, with an adjustable threshold value, and to output a count signal on this basis. A pixel-electronics module can also have a counting element which is designed to count a number of count signals, i.e. essentially instances in which a threshold value is exceeded in the comparator. The counting element can be designed as an incremental counter, for example. The digital pixel-measurement signal can then be based on the number counted by the counting element, for example. The digital pixel-measurement signal can correspond to a counter value of the counting element. Based upon such a counter value, it is possible to infer the intensity of incident x-radiation. Such a design of a pixel-electronics module is generally associated with a direct-conversion x-ray detector.

In this case, a respective pixel-electronics module can also comprise a plurality of comparators with adjustable threshold values and counting elements. This can allow an energy-resolved measurement of the incident x-radiation. If the pixel-electronics module comprises a plurality of comparators and respective counting elements coupled thereto, and therefore provides a plurality of digital pixel-measurement signals, e.g. in the form of counter values of the plurality of counting elements, a signal-processing unit of one of the multiplicity of pixel-electronics modules can be designed to adapt each of the digital pixel-measurement signals or only a subset of the digital pixel-measurement signals.

By contrast, in the case of an indirect-conversion x-ray detector, use is often made of integrating pixel-electronics modules in which the energy deposition of photons arriving during a readout time window is integrated in a respective pixel-electronics module. The digital pixel-measurement signal of a respective pixel-electronics module can then be based on the digitized integrated value, for example.

The inventive digital signal-processing unit of at least one embodiment of a pixel-electronics module of the multiplicity of pixel-electronics modules can comprise one or more plurality of digital circuit elements designed to execute an operation (also referred to below as an adaptation operation) which, based upon a digital pixel-measurement signal, adapts the digital pixel-measurement signal so that an adapted digital pixel-measurement signal can then be provided.

An adaptation operation can comprise e.g. an arithmetic operation or a combination of arithmetic operations. For example, this can be an (in particular also weighted) addition, subtraction, division, multiplication, the application of an exponential function or similar. The adaptation operation can also comprise a logic operation, e.g. a comparison, a conjunction, a negation or similar.

In addition to the digital pixel-measurement signal that is to be adapted, at least one further adaptation parameter can be entered into an adaptation operation of the signal-processing unit. An adaptation parameter can comprise e.g. a weighting factor, a decay time constant of an exponential function, a summand, a comparison parameter or similar. An adaptation parameter which can be entered into an adaptation operation of the signal-processing unit can also be based on a measurement value that is measured via the x-ray detector or a sensor associated therewith. This can be e.g.

one or a plurality of previously measured pixel-measurement signals of the pixel-electronics module, one or a plurality of pixel-measurement signals of one or a plurality of adjacent pixel-electronics modules, or also another measurement value such as a temperature measurement value or a time measurement value.

A digital signal-processing unit according to at least one embodiment of the invention is designed to be settable. The settable nature of the digital signal-processing unit can allow the signal-processing unit of a pixel-electronics module, or the adaptation operation that is executed by the signal-processing unit, to be adjustable, i.e. adaptable, by a user, even after implementation in the pixel-electronics module. This can include the signal-processing unit being parameterizable, configurable and/or programmable.

For example, this includes the possibility of defining variables or transfer values for an adaptation operation, the variables or transfer values being processed by the signal-processing unit for the execution of the adaptation operation. This can also include specifying which variables or transfer values should be entered into an adaptation operation of the signal-processing unit. For example, this can also include specifying whether an adaptation operation is based on a previously measured pixel measurement value or a temperature measurement value. This can include the storage in an adaptable manner of e.g. standard values for adaptation parameters (also referred to below as adaptation coefficients), and using these as standard when executing the adaptation operation. This can also include the possibility of storing a plurality of sets of standard values or a standard value, which can then be selected for the adaptation operation via the signal-processing unit. The settable nature of the digital signal-processing unit can then allow the selection of such a set. The availability of previously specified sets of adaptation parameters can allow rapid and simple adaptation of the signal-processing unit to current operating conditions.

For this purpose, transfer values can be stored in a settable storage element for adaptation parameters in the evaluation unit in a step of adjusting the evaluation unit, or respectively current transfer values can be stored for retrieval in a storage element, e.g. when using a measurement value that is measured in temporal proximity to an adaptation.

The settable nature can also allow an interconnection of one or a plurality of circuit elements of the digital signal-processing unit to be adapted. For example, a circuit element can be selected from a plurality of circuit elements of the signal-processing unit for the purpose of adapting a digital pixel-measurement signal. This can be achieved by virtue of configuration parameters of the signal-processing unit being adaptable, and specifying the interconnection of a plurality of circuit elements of the signal-processing unit. Here likewise, provision can be made for a plurality of sets of configuration parameters or one configuration parameter to be stored in a storage element in the evaluation unit, and for the settable nature to allow the selection of a configuration parameter set.

Programming can include defining a sequence of operations, e.g. in the form of program code, which can then be implemented by the signal-processing unit according to the defined sequence. For example, a program code comprising instructions for the performance of an operation or a sequence of operations can be stored in a program store of the evaluation unit, wherein the operation or operations can then be executed based upon the instructions by a circuit element, e.g. a suitably configured arithmetic-logic unit in the pixel-electronics modules.

In this case, the selection of the adaptation parameters and/or the operations to be executed for the purpose of adapting a digital pixel-measurement signal in the pixel-electronics modules of the multiplicity of pixel-electronics modules can be based on experimental prior knowledge or on calibration measurements. In this case, the experimental prior knowledge can include which adaptation of the digital pixel-measurement signals is necessary in order to obtain an improved adapted digital pixel-measurement signal and therefore to generate a measurement data record of higher quality.

The digital signal-processing units of the multiplicity of pixel-electronics modules can be designed to be individually settable, such that each digital signal-processing unit can be adjusted individually and if applicable differently from any other pixel-electronics module of the multiplicity. The digital signal-processing units of the multiplicity of pixel-electronics modules can also be settable in a broadscale manner and only within a group comprising a plurality of pixel-electronics modules, so that the signal-processing units can be adjusted in a coordinated and uniform manner at least within this group. In this case, the group can comprise the entire multiplicity of pixel-electronics modules. The multiplicity of pixel-electronics modules can however be divided into a plurality of groups.

For the purpose of setting, the evaluation unit can comprise a control-data input by which the digital signal-processing units of the pixel-electronics modules of the multiplicity of pixel-electronics modules, or associated storage elements, can be set and adapted individually or in a broadscale manner in a group. For example, provision can be made for setting the signal-processing units via an external computing unit which is coupled to the control-data input of a respective evaluation unit via a control data line and allows parameters or program code to be transferred, adapted or selected.

By way of the digital signal-processing unit provided in the pixel-electronics modules, it is advantageously possible already to perform an adaptation of the pixel-measurement signals in the pixel-electronics modules and before a readout from the evaluation unit. This can advantageously be used to correct the pixel-measurement signals. For example, time-dependent, temperature-dependent or radiation-dependent drift effects can already be corrected or at least reduced in the pixel-electronics modules. The pixel-oriented adaptation, particularly when implemented in an ASIC, can provide a particularly efficient means of correcting the digital pixel-measurement signals. In particular, correction in an ASIC can be significantly more efficient than subsequent corrections based on processing by FPGAs or similar processing units. In this case, the adaptation can advantageously be adapted based upon the current operating conditions or based upon a selected application routine for an application of an x-ray detector comprising the evaluation unit.

According to a design variant of the evaluation unit, the digital signal-processing unit of a respective pixel-electronics module has a measurement value store into which the digital pixel-measurement signal can be transferred. The digital signal-processing unit is then designed to adapt the digital pixel-measurement signal that has been transferred into the measurement value store.

The adaptation and the generation of the digital pixel-measurement signals can advantageously be separated, so that during an adaptation of a digital pixel-measurement signal, a pixel-measurement signal can already be generated again. It is advantageously possible to avoid dead time of a respective pixel-electronics module for the capture of electrical signals from the converter unit.

A storage element that is designed as a measurement value store in this case can also be designed to store more than one digital pixel-measurement signal.

Furthermore, in a design variant of the evaluation unit, the digital signal-processing unit can be designed to adapt a current digital pixel-measurement signal based upon at least one previously processed digital pixel-measurement signal.

For this purpose, the digital signal-processing unit can have a storage element for at least one digital pixel-measurement signal that was previously processed by the pixel-electronics module, and the digital signal-processing unit can be designed to adapt the current digital pixel-measurement signal based upon the at least one previously processed digital pixel-measurement signal. Previous pixel-measurement signals can be used to derive a time-dependency of the pixel-measurement signals, for example.

Furthermore, in a design variant of the evaluation unit, the digital signal-processing unit can be designed to adapt a current digital pixel-measurement signal based upon at least one digital pixel-measurement signal of an adjacent pixel-electronics module.

For this purpose, the digital signal-processing unit can have a storage element for at least one digital pixel-measurement signal of an adjacent pixel-electronics module, and the digital signal-processing unit can be designed to adapt the currently processed pixel-measurement signal based upon the at least one digital pixel-measurement signal of the adjacent pixel-electronics module. The pixel-electronics modules are designed in such a way that a pixel-measurement signal of an adjacent pixel-electronics module can be transferred into the storage element. A correlated adaptation can be achieved based upon adjacent pixel-measurement signals.

The signal-processing unit can also be designed to adapt a current digital pixel-measurement signal based upon more than one previously processed digital pixel-measurement signal or based upon more than one digital pixel-measurement signal of an adjacent pixel-electronics module or a plurality of adjacent pixel-electronics modules. A storage element as described above can be designed accordingly to store more than one of these pixel-measurement signals.

According to a further design variant of the evaluation unit, the digital signal-processing unit comprises a digital circuit element from the following list an adding element, a multiplying element, a dividing element, a calculation element for an exponential function, a multiplexer.

It is advantageously possible to perform adaptations based on addition, multiplication, division, or an exponential function. A multiplexer can advantageously allow circuit elements of the signal-processing unit to be interconnected in a simple manner.

The digital signal-processing unit can comprise a plurality of circuit elements. An interconnection of the circuit elements can then be designed to be configurable in particular. Provision is thus made for allowing the signal-processing unit, and the adaptation produced thereby, to be compatible with operating conditions or an application routine.

The digital signal-processing unit can also comprise a storage element for at least one adaptation parameter or at least one configuration parameter for adjusting the signal-processing unit. For example, transfer values and adaptation coefficients for adaptation operations can be stored in the storage element. A configuration parameter can include a parameter relating to an interconnection of the signal-processing unit. In particular, the storage element can be settable and therefore adaptable, such that the adaptation parameter or configuration parameter can be changed and adapted by a user and the digital signal-processing unit can be adjusted.

Furthermore, in the evaluation unit, a storage element for at least one adaptation parameter or configuration parameter can be designed in a broadscale manner for the purpose of adjusting the digital signal-processing units of a plurality of pixel-electronics modules.

In this way, the digital signal-processing units within a group of pixel-electronics modules comprising a plurality of pixel-electronics modules can be designed to be settable in a broadscale manner, so that the signal-processing units can be adjusted in a coordinated and uniform manner at least within this group. The group in this case can comprise the entire multiplicity or just a subset of the multiplicity of pixel-electronics modules. Simplified adjustment of the multiplicity of pixel-electronics modules is advantageously possible in this case.

A storage element can be embodied as a storage block or a register, e.g. a so-called D flip-flop.

According to a variant of the evaluation unit, the digital signal-processing unit of a respective pixel-electronics module can comprise a processor core with an arithmetic-logic unit (ALU).

An ALU is an electronic arithmetic-logic unit. An ALU is designed to calculate arithmetic and logic functions. It is generally able to perform at least minimal operations comprising addition, negation or conjunction. It can also be designed to perform operations comprising subtraction, multiplication, division, comparison operations, disjunction, contravalence and others.

It is also advantageously possible to perform more complex adaptation operations, also based on a sequence of a plurality of instructions in particular.

The evaluation unit can comprise a program store which holds a program code for setting the ALU. The program store can be provided in each pixel-electronics module of the multiplicity of pixel-electronics modules. The program store can also be designed in a broadscale manner for the digital signal-processing units of a plurality of pixel-electronics modules. A program store can be programmed or configured, in particular by a control-data input of the evaluation unit, so that the operations performed by the digital signal-processing units can easily be adapted.

In particular, a program store that is designed in a broadscale manner can be designed in conjunction with a storage element for at least one adaptation parameter that is designed in a broadscale manner.

The control of the processor cores in the pixel-electronics modules of the multiplicity of pixel-electronics modules can be implemented in accordance with the principle of Single Instruction Multiple Data (SIMD). As a result, the same operation can be performed concurrently on a plurality of data items, here the pixel-measurement signal or pixel-measurement signals of the pixel-electronics modules.

Time-efficient programming and parallel execution of the adaptation operations can advantageously be implemented easily on all pixel-electronics modules.

Furthermore, at least one embodiment of the invention relates to an x-ray detector comprising an evaluation unit as per at least one embodiment of the invention and a converter unit, wherein each pixel-electronics module of the multiplicity of pixel-electronics modules is coupled in an electrically conductive manner to the converter unit for the purpose of signaling, in order to feed electrical signals into the pixel-electronics module.

The x-ray detector can also comprise a plurality of evaluation units. The plurality of evaluation units can be coupled to a converter unit or a plurality of converter units. The use of evaluation units having a small area can be appropriate for a more economical implementation. Using a plurality of evaluation units and/or a plurality of converter units, it is possible to achieve x-ray detectors having a larger area than is possible using one unit alone.

All of the embodiment variants described above in connection with the inventive evaluation unit of at least one embodiment can also be realized correspondingly in the x-ray detector. The description in relation to the evaluation unit and the advantages of the evaluation unit described above can be transferred to the x-ray detector correspondingly.

Furthermore, at least one embodiment of the invention relates to a medical imaging device comprising at least an x-ray detector of at least one embodiment with an evaluation unit, and an x-ray source which is situated opposite the x-ray detector and is designed to expose the x-ray detector to x-radiation.

For the purpose of recording the x-ray image record, the object to be depicted can be placed between the x-ray source and the x-ray detector and irradiated via the x-ray source.

In particular, the medical imaging device can be designed as a computed tomography apparatus. The medical imaging device can be designed as a SPECT or PET system. However, it can also be designed as e.g. a C-arm x-ray apparatus and/or DynaCT or otherwise.

All of the embodiment variants described above in connection with the inventive evaluation unit can also be realized in the medical imaging device comprising an x-ray detector with an evaluation unit according to at least one embodiment of the invention. The description in relation to the evaluation unit and the advantages described above can also be transferred to the inventive medical imaging device correspondingly.

At least one embodiment of the invention further relates to a method for operating an x-ray detector according to one of the embodiments described above. The method comprises the steps of the exposure, the processing and the adaptation.

In at least one embodiment, in the step of the exposure, the converter unit of the x-ray detector is exposed to x-radiation via an x-ray source, thereby generating electrical signals in the converter unit which are fed into the multiplicity of pixel-electronics modules of the evaluation unit via the electrically conductive coupling.

In at least one embodiment, in the step of the processing, the electrical signals that have been fed in are processed via a respective pixel-electronics module of the multiplicity of pixel-electronics modules to form a digital pixel-measurement signal.

In at least one embodiment, in the step of the adaptation, at least one digital pixel-measurement signal is adapted in a pixel-electronics module of the multiplicity of pixel-electronics modules via the settable digital signal-processing unit of the pixel-electronics module.

In at least one embodiment, by virtue of the step of the adaptation, a correction of the pixel-measurement signal can be performed such that an improved data record of digital pixel-measurement signals can be provided based upon the adapted pixel-measurement signals. Based upon an improved data record, it is then possible to generate an improved x-ray image record having higher image quality.

In at least one embodiment, the method can also comprise the step of adjusting the evaluation unit. The adjustment can include parameterizing, configuring and/or programming at least one settable digital signal-processing unit and/or a storage element associated therewith. The adjustment can include adapting an adaptation parameter, a configuration parameter or program code for the execution of an adaptation operation by the digital signal-processing unit.

In this case, the advantages of at least one embodiment of the inventive evaluation unit and design variants thereof can likewise be transferred directly to the method for operating an inventive x-ray detector which comprises an inventive evaluation unit as per one of the embodiment variants described above.

In the context of embodiments of the invention, it is moreover possible to combine features that are described in relation to different embodiment variants of the invention and/or different statutory classes of claim (method, use, device, system, arrangement, etc.) to form further embodiment variants of the invention. For example, a claim which relates to a device can also be developed by features that are described or claimed in connection with a method, and vice versa. Functional features of a method can be embodied by e.g. material components that are designed correspondingly. In addition to the embodiment variants of the invention that are explicitly described in this application, a wide variety of further embodiment variants of the invention are conceivable which a person skilled in the art can arrive at without thereby departing from the scope of the invention as specified in the claims.

The use of the indefinite article "a" or "an" does not preclude multiple instances of the feature concerned. The use of the expression "to have" does not preclude the possibility that the terms associated by the expression "to have" are identical. For example, the medical imaging device has the medical imaging device. The use of the expression "unit" does not preclude the subject matter to which the expression "unit" relates from having a plurality of components which are spatially separated from each other.

The expression "based upon" can, in the context of the present application, be understood in particular in the sense of the expression "using". In particular, wording according to which a first feature is generated (or alternatively: determined, identified, etc.) based upon a second feature does not preclude the possibility of the first feature being generated (or alternatively: determined, identified, etc.) based upon a third feature.

FIG. 1 shows an example arrangement of a plurality of x-ray detectors 2 according to an example design variant. The x-ray detectors 2 in this arrangement are arranged in the form of a matrix in order to produce a larger overall area for detecting x-radiation. Other arrangements of one or a plurality of x-ray detectors are also possible.

By way of example, FIG. 1 shows a direct-conversion x-ray detector 2, having a converter unit 3 with a direct-conversion converter material. The converter material can be CdTe, CZT, CdZnTeSe, CdTeSe, CdMnTe, InP, TlBr$_2$, HgI$_2$, GaAs, Si or other suitable material, for example. The top side of the converter element 3 has a first electrode 71 (top electrode). The underside of a respective converter unit 3 has sensor pixel electrodes 55. The sensor pixel electrodes 55 are connected to the evaluation unit 1 via the electrically conductive connections 69 and the evaluation pixel electrodes 57.

The evaluation unit 1 can be designed in the form of an ASIC in particular. The electrically conductive connections 69 can be designed as bump bonds or solder material in connection with copper pillars, for example, or otherwise. The evaluation unit 1 is coupled to the converter unit 3 via the sensor pixel electrodes 55, the electrically conductive connections 69 and the evaluation pixel electrodes 57 for the purpose of signaling.

An electrical field can be applied between the first electrode 71 and the respective sensor pixel electrodes 57, wherein the electrical field defines a sensitive detection volume in the converter element 3 in each case, and the sensitive detection volume is assigned to an evaluation pixel electrode 57. The electrical signal generated by an energy deposition in such a detection volume as a result of incident x-ray photons can then be fed via the assigned electrically conductive connection 69 and the evaluation pixel electrode 57 into the evaluation unit 1 and in particular into a signal input of a pixel-electronics module 5 of the evaluation unit 1.

The evaluation unit 1 in the example shown is moreover arranged on a substrate 61 and is connected e.g. by way of TSV (through silicon via) connections 63 through the substrate 61 to a peripheral electronics module 65.

An x-ray detector according to an embodiment of the invention can also be constructed in a manner which differs from the example illustration in FIG. 1. In particular, the x-ray detector 1 can also be designed as an indirect-conversion x-ray detector comprising an indirect-conversion converter unit. Here and in the following FIGS. 2 to 4, for illustrative purposes, reference is made by way of example to a counting direct-conversion x-ray detector. However, a person skilled in the art can easily apply the example embodiment variants to an indirect-conversion x-ray detector and integrating x-ray detector.

The evaluation unit 1 of the x-ray detector 2 has a plurality of pixel-electronics modules 5. The pixel-electronics modules 5 are designed to process the electrical signals that are fed into a respective pixel-electronics module 5 from the converter unit 3, and produce a digital pixel-measurement signal.

In the example shown, the number of sensor pixel electrodes 55, the number of conductive connections 69, the number of evaluation pixel electrodes 57 and the number of pixel-electronics modules 5 in the evaluation unit 1 are equal. However, other designs are also possible.

According to an embodiment of the invention, the evaluation unit 1 has a multiplicity of pixel-electronics modules 5, each of the pixel-electronics modules 5 having at least one settable digital signal-processing unit 7 which is designed to adapt a processed digital pixel-measurement signal in a respective pixel-electronics module of the multiplicity of pixel-electronics modules 5.

The multiplicity of pixel-electronics modules 5, each comprising a digital signal-processing unit 7, can correspond to the plurality of pixel-electronics modules 5 described above. In other words, each of the pixel-electronics modules 5 of the plurality can also be part of the multiplicity of pixel-electronics modules 5. However, other designs are also possible.

A respective pixel-electronics module 5 of the multiplicity of pixel-electronics modules of the evaluation unit 1 can comprise analog and digital circuit elements. The pixel-electronics modules 5 of the multiplicity of pixel-electronics modules 5 are designed at least to receive an electrical signal from a converter unit 3 via at least one signal input and to digitize an electrical signal that has been fed in, such that, based upon the processing of a signal that has been fed in from a coupled converter unit 3, a digital pixel-measurement signal can be provided in a pixel-electronics module. The inventive digital signal-processing unit 7 of the pixel-electronics module 5 can comprise one or a plurality of digital circuit elements which is or are designed to execute, based upon a digital pixel-measurement signal, an adaptation operation which adapts the digital pixel-measurement signal, such that a digital pixel-measurement signal which has been adapted by the signal-processing unit 7 can then be provided by the pixel-electronics module 5. The adaptation operation can comprise an arithmetic or logic operation.

The digital signal-processing unit 7 of a respective pixel-electronics module 5 of the multiplicity of pixel-electronics modules 5 is designed to be settable in the sense that it can be parameterized, configured and/or even programmed, and therefore the signal-processing unit 7 or the adaptation operation performed thereby can be adjusted and adapted.

The digital signal-processing units 7 of the multiplicity of pixel-electronics modules 5 can be designed to be individually settable, such that each digital signal-processing unit 7 can be adjusted individually and if applicable differently from the signal-processing unit 7 of any other pixel-electronics module 5 of the multiplicity. The digital signal-processing units 7 of the multiplicity of pixel-electronics modules can also be settable in a broadscale manner and only in a group of pixel-electronics modules 5, so that the signal-processing units 7 can be adjusted in a coordinated and uniform manner at least within this group.

Figure 2:
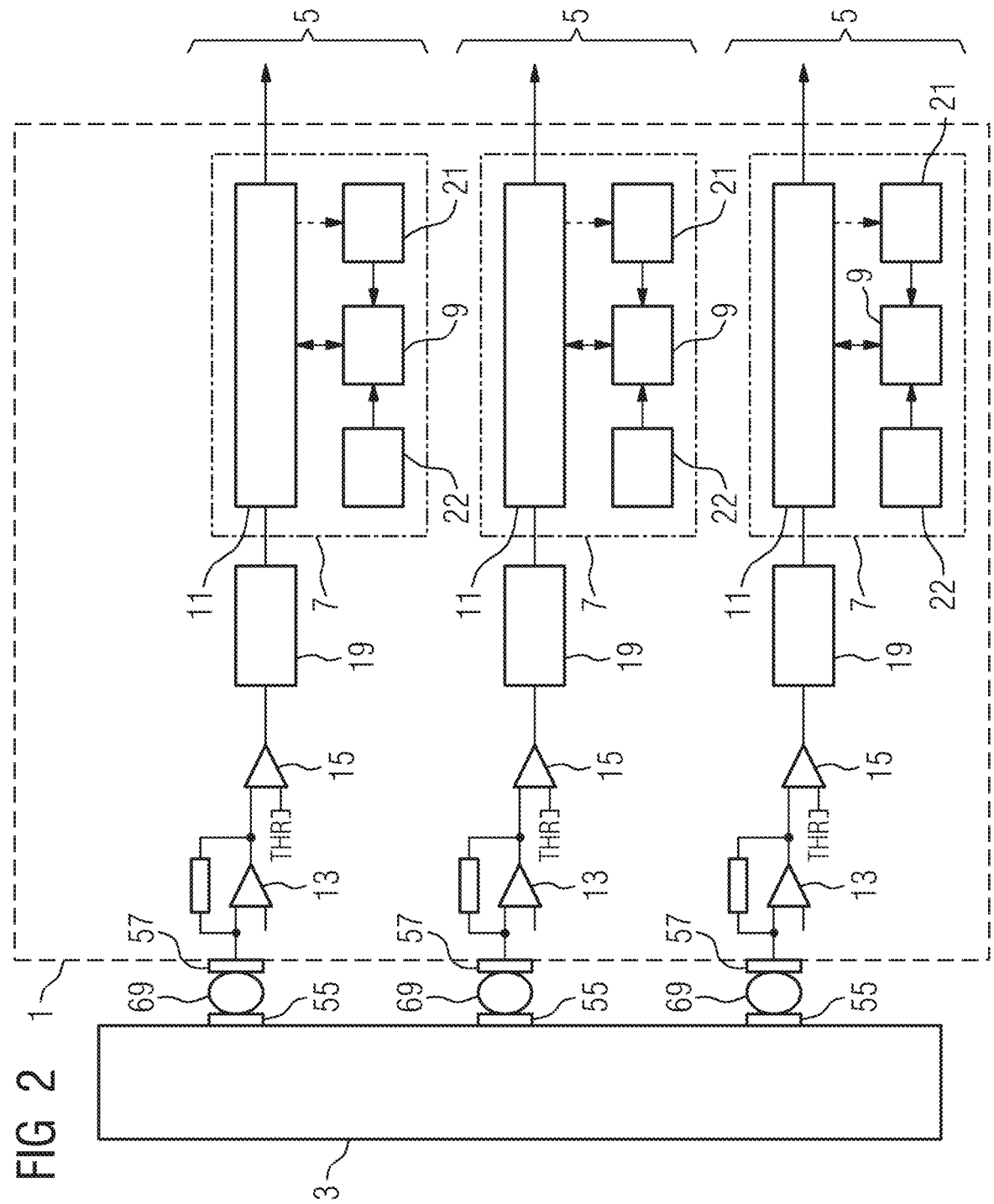
FIG. 2 shows a schematic illustration of a first design variant of a signal-processing unit in an evaluation unit.

FIG. 2 shows a purely schematic illustration of a first design variant of a signal-processing unit 7 in an evaluation unit 1 of an x-ray detector 2 as illustrated by way of example in FIG. 1.

For the purposes of illustration, only three pixel-electronics modules 5 of an evaluation unit 1 are shown in this case, each being coupled via an electrically conductive connection to the converter unit 5. In particular, each pixel-electronics module has a signal input for feeding in electrical signals.

As mentioned above in the context of the description of FIG. 1, reference is made here to a photon-counting direct-conversion x-ray detector. However, transfer to an integrating and/or indirect-conversion x-ray detector is readily possible.

In the example shown, attached to a respective signal input of a pixel-electronics module 5, the signal input being coupled to the converter unit 3, are a signal amplification unit 13 and a comparator 15 with an adjustable threshold value THR. An electrical signal which is fed in from the converter unit and is based on an energy deposition of an x-ray photon in the converter material is amplified in the signal amplification unit. As a rule, the amplified signal is also shaped into a voltage pulse via a pulse shaper. The amplified signal is compared with an adjustable threshold value THR via the comparator 15, a binary count signal being output if the threshold value is exceeded. The binary count signal can then be counted via the counting element 19, this being designed as an incremental counter, for example. The counting element 19 provides the digital pixel-measurement signal in the form of its counter value here, and the digital pixel-measurement signal is then adapted via the digital signal-processing unit 7. In other design variants, further elements can also be provided in the pixel-electronics module.

In the embodiment variant shown, the digital signal-processing unit 7 of a respective pixel-electronics module 5 comprises a measurement value store 11 to which the digital pixel-measurement signal can be transferred. In other words, the counter value of the counting element can be transferred to the measurement value store 11.

The digital signal-processing unit 7 is then designed to adapt the pixel-measurement signal that has been transferred to the measurement value store 11. For this purpose, the signal-processing unit 7 comprises a circuit element 9 which is designed to execute an operation based upon the digital pixel-measurement signal stored in the measurement value store 11.

The signal-processing unit 7 can comprise, for example, an adding element, a multiplying element, a dividing element, a calculation element for an exponential function or other type of digital circuit element 9 as a digital circuit element 9. In particular, provision can also be made for a plurality of variously designed digital circuit elements 9 which can perform different operations for the purpose of adapting the digital pixel-measurement signal. In particular, the interconnection of the circuit elements 9 can be designed such that it can be configured by adapting configuration parameters. This can allow selection of an operation or even a configurable series of operations. To this end, provision can be made for e.g. a multiplexer or a plurality of multiplexers or a network for interconnecting the circuit elements 9 in the signal-processing unit 7. Likewise, provision can be made for a storage element for at least one configuration parameter which can be retrieved for a configuration of the signal-processing units.

In the embodiment shown, the signal-processing unit 7 also comprises a storage element 22 for at least one adaptation parameter. An adaptation parameter stored in a storage element 22 can be e.g. a weighting factor, a decay time constant of an exponential function, a summand, a comparison parameter or similar, which is entered into the adaptation operation of the signal-processing unit. The storage element 22 is designed to be settable in particular, such that the at least one adaptation parameter in the storage element 22 can be adapted.

The signal-processing unit 7 also has a storage element 21 for at least one digital pixel-measurement signal that was previously processed by the pixel-electronics module 5. A plurality of adaptation parameter values can be stored in the storage element. An adaptation parameter can be selected for the adaptation operation as a function of at least the pixel-measurement signal.

The digital signal-processing unit 7 shown can be designed to adapt a current digital pixel-measurement signal that has been transferred into the measurement value store 11 based upon at least one previously processed digital pixel-measurement signal from the storage element 21 and based upon the at least one adaptation parameter which is stored in the storage element 22. The previously measured pixel-measurement signal can be transferred into the storage element 21 in each case before adaptation of the previously measured pixel-measurement signal, for example, and then entered into the adaptation of a currently measured pixel-measurement signal. The storage element 21 can also be designed in particular to store more than one previously measured digital pixel-measurement signal.

Alternatively or additionally, a storage element in the signal-processing unit 7 can also be designed for at least one digital pixel-measurement signal of an adjacent pixel-electronics module 5. The digital signal-processing unit 7 can be designed to adapt a current digital pixel-measurement signal based upon at least one digital pixel-measurement signal of an adjacent pixel-electronics module 5. The storage element can be designed to store digital pixel-measurement signals from a plurality of adjacent pixel-electronics modules 5. The pixel-electronics modules 5 can be so designed or so interconnected for the purpose of signaling that a transfer of the pixel-measurement signals is enabled between the pixel-electronics modules 5, i.e. so that a digital pixel-measurement signal of an adjacent pixel-electronics module can be transferred into a storage element of the pixel-electronics module concerned.

An adaptation parameter for an adaptation operation can be selected as a function of a pixel-measurement signal of an adjacent pixel-electronics module 55 or as a function of a previously measured pixel-measurement signal.

In the example shown, all pixel-electronics modules 5 are of identical design. However, different designs are also possible.

Following an adaptation of the digital pixel-measurement signal, the adapted pixel-measurement signal can be output or read out.

In the illustration, only one comparator 15 and one counting element 19 are shown. In other embodiment variants, each signal input can also be provided with a plurality of comparators 15 having an adjustable threshold THR in each case, with counting elements 19 coupled thereto in each case, such that a plurality of digital pixel-measurement signals are provided in each pixel-electronics module 5 on this basis. If a plurality of digital pixel-measurement signals are provided by a pixel-electronics module 5, the signal-processing unit 7 can be designed to adapt all or only a subset of the digital pixel-measurement signals.

Figure 3:
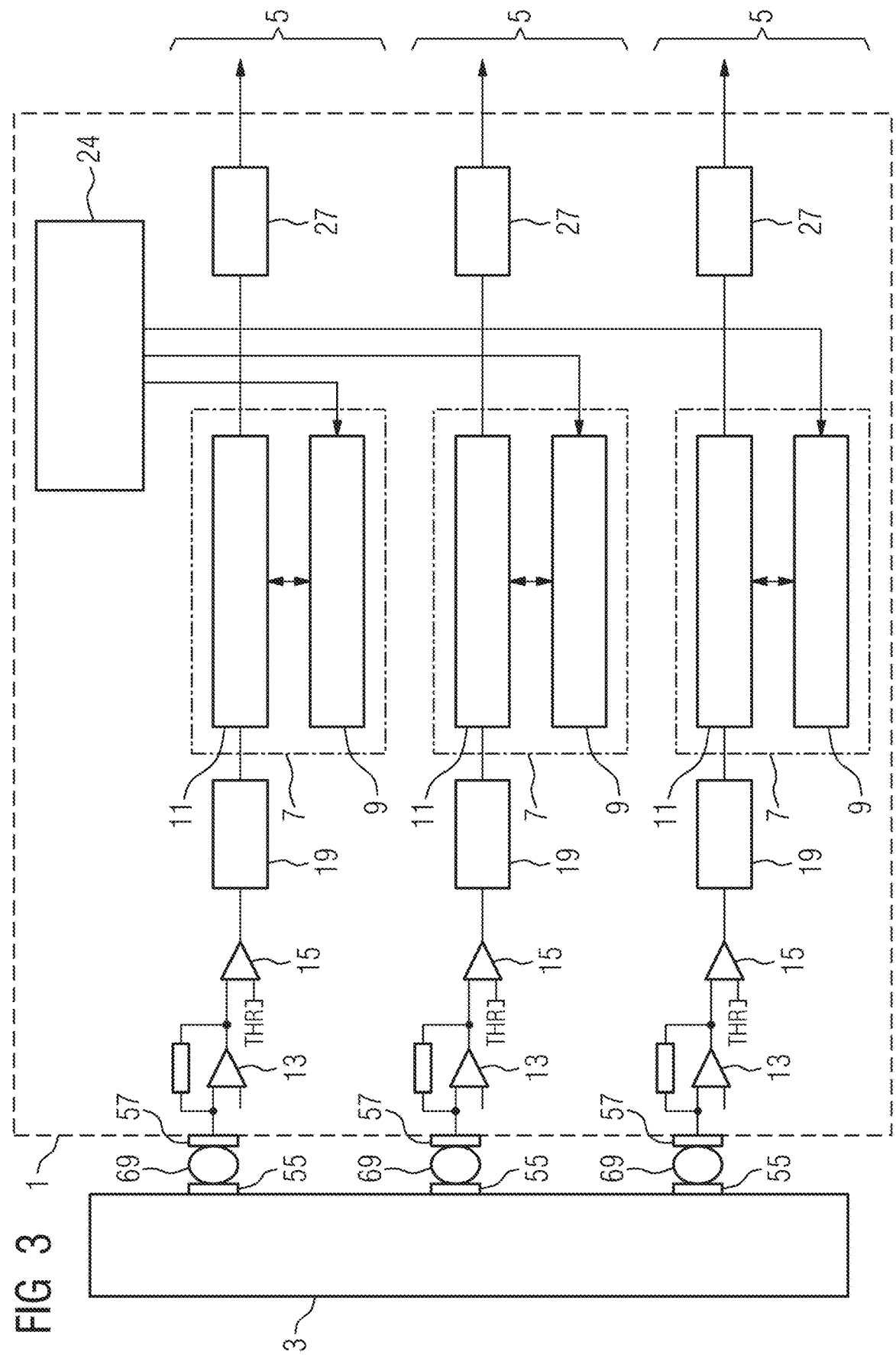
FIG. 3 shows a schematic illustration of a second design variant of a signal-processing unit in an evaluation unit.

FIG. 3 shows a further design variant of a signal-processing unit 7 of an evaluation unit 1.

In this case, for the purposes of illustration, only one circuit element 9 and one measurement value store 11 are depicted. However, further circuit elements 9 and/or storage elements can be provided in addition to these. Furthermore, in the evaluation unit 1, a storage element 24 for at least one adaptation parameter or configuration parameter is designed in a broadscale manner for the purpose of adjusting the digital signal-processing units 7 of a plurality of pixel-electronics modules 5.

In other words, in the case shown here, a storage element for at least one adaptation parameter or at least one configuration parameter is not provided for each signal-processing unit 7, but is instead provided for at least a group of signal-processing units 7 jointly. The parameter or parameters from the broadscale storage element 24 can then be entered into the configuration of the signal-processing unit 7 or the adaptation operation of the digital pixel-measurement signal for all pixel-electronics modules 5 of the group of pixel-electronics modules 5 equally. The group can comprise the entire multiplicity of pixel-electronics modules 5 of the evaluation unit 1. Provision can also be made for a plurality of groups, however, each having an assigned broadscale storage element 24.

A respective pixel-electronics module 5 also comprises a further readout storage element 27 to which the adapted pixel-measurement signal can be output, i.e. essentially copied, from the measurement value store 11 of the signal-processing unit 7. The adapted digital pixel-measurement signal can be read out from the readout storage element 27.

In this way, the readout can be separated from the adaptation of the digital pixel-measurement signals in the signal-processing unit 7. Dead times can advantageously be avoided in this way.

Figure 4:
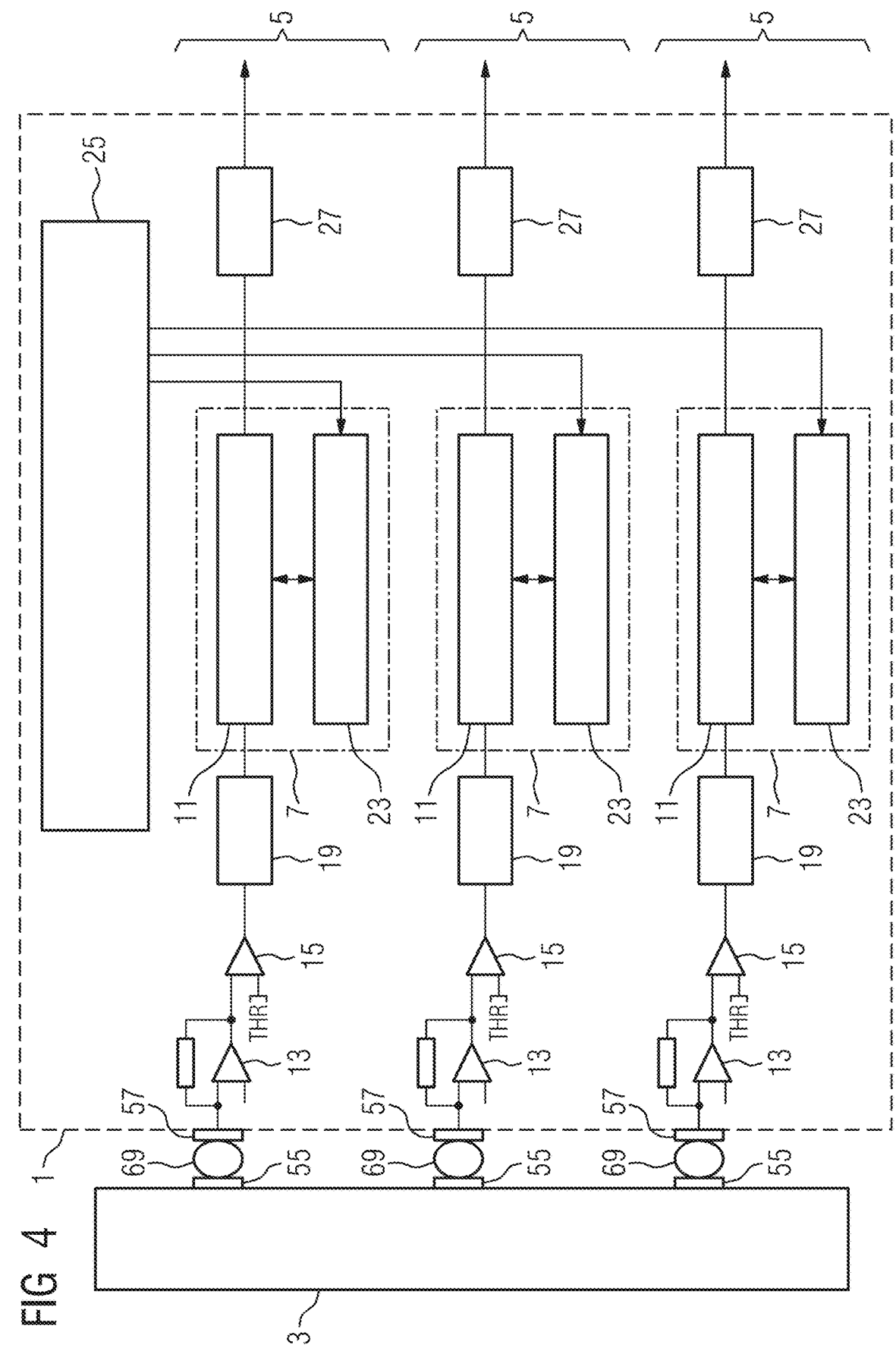
FIG. 4 shows a schematic illustration of a third design variant of a signal-processing unit in an evaluation unit.

FIG. 4 shows a further design variant of a signal-processing unit 7.

In this variant, the digital signal-processing unit 7 comprises a processor core 23 with an arithmetic-logic unit (ALU).

In addition, the evaluation unit 1 comprises a program store 25 which holds a program code for setting a processor core 23 of a signal-processing unit 7 of a pixel-electronics module of the multiplicity of pixel-electronics modules 5.

In the variant shown, the program store 25 is designed in a broadscale manner for the digital signal-processing units 7 of a plurality of pixel-electronics modules 5.

In addition to the program store 25, a storage element (not shown in the illustration) for at least one adaptation parameter can also be provided, preferably likewise in a broadscale manner for a plurality of pixel-electronics modules 5, for adaptation parameters which are entered into the adaptation of a digital pixel-measurement signal by the ALU.

The control of the processor cores in the pixel-electronics modules of the multiplicity of pixel-electronics modules can be implemented in accordance with the principle of Single Instruction Multiple Data (SIMD). As a result, the same operation can be performed concurrently on a plurality of data items, here the pixel-measurement signal or pixel-measurement signals of the pixel-electronics modules.

Figure 5:
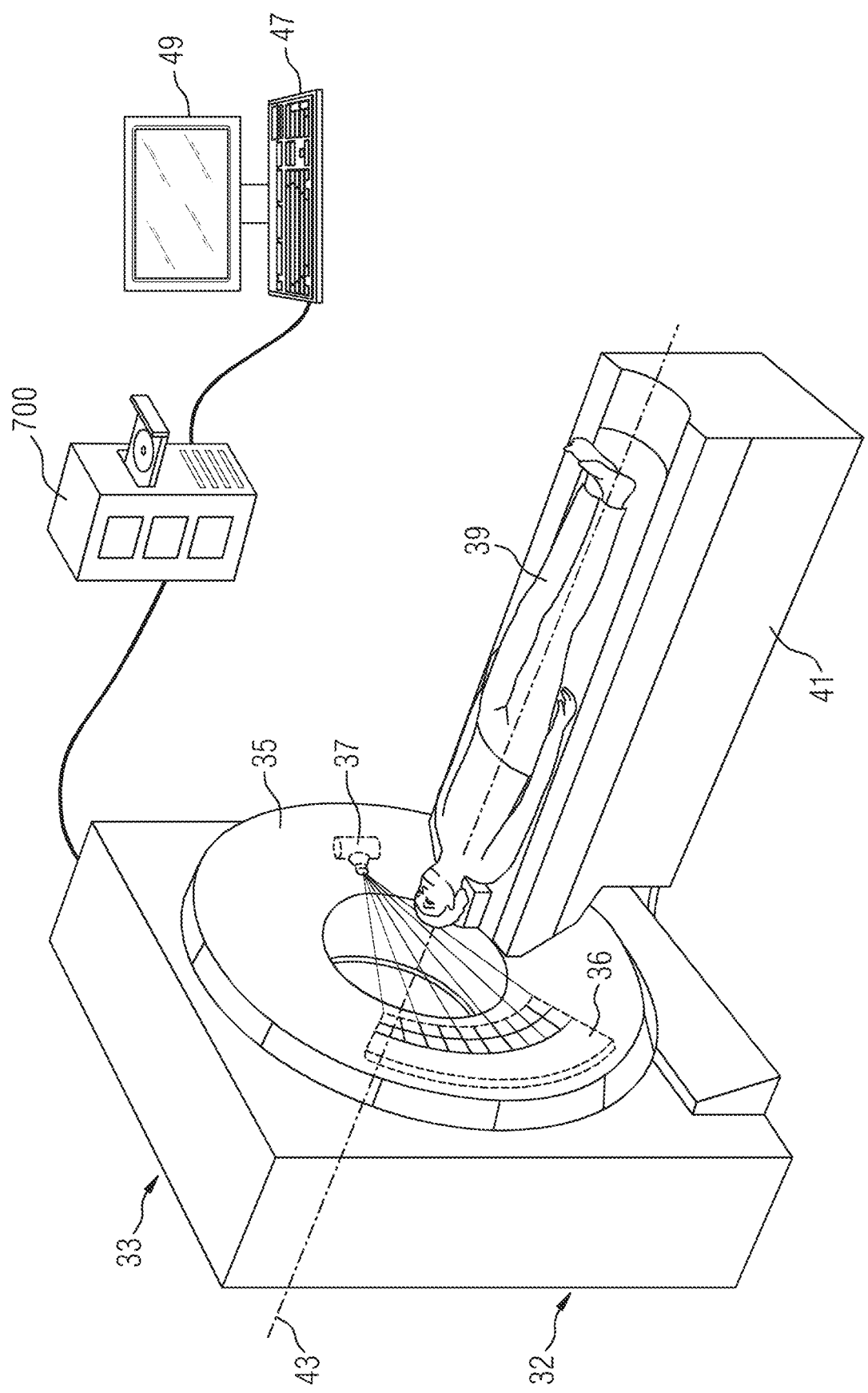
FIG. 5 shows an example embodiment variant of a medical imaging device.

FIG. 5 shows an example embodiment variant of a medical imaging device 32, with a detection unit 36 comprising at least one x-ray detector 2 according to an embodiment of the invention and an x-ray source 37 which is situated opposite the detection unit 36. The x-ray source 37 is designed to expose the detection unit 36 and therefore a converter unit 3 of the x-ray detector 2 to x-radiation. The medical imaging device 32 shown is designed as a computed tomography apparatus in particular. The computed tomography apparatus comprises a gantry 33 with a rotor 35. The rotor 35 comprises the x-ray source 37 and the detection unit 36. The rotor 35 can be rotated about the rotation axis 43. The examination object 39, here a patient, is supported on the patient couch 41 and can be moved through the gantry 33 along the rotation axis 43. In general, the object 39 can be an animal and/or a human patient, for example. The computing unit 700 is provided for the purpose of controlling the medical imaging device and/or generating an x-ray image record based upon the pixel-measurement signals that have been processed and adapted by the x-ray detector 2.

In the case of a computed tomography apparatus, a (raw) x-ray image record of the object is usually recorded from a multiplicity of angles via at least one x-ray detector 2, the x-ray image record being based on processed electrical pixel-measurement signals of the pixel-electronics modules 5 of the evaluation unit 1. A final x-ray image record can then be reconstructed based upon the (raw) x-ray image record by way of a mathematical method, e.g. comprising a filtered back-projection or an iterative reconstruction method.

The computing unit 700 can comprise a control unit for controlling the medical imaging device 32 and a generation unit 55 for generating an x-ray image record based upon pixel-measurement signals. The computing unit 700 can be designed to set (i.e. configure, parameterize or program) the settable digital signal-processing units 7 in the pixel-electronics modules 5, or elements (e.g. storage elements) which are provided in a broadscale manner for a plurality of pixel-electronics modules 5.

Furthermore, an input device 47 and an output device 49 are connected to the computing unit 700. The input device and the output device can allow e.g. interaction with a user, e.g. a manual configuration, a confirmation or triggering of a method step.

Figure 6:
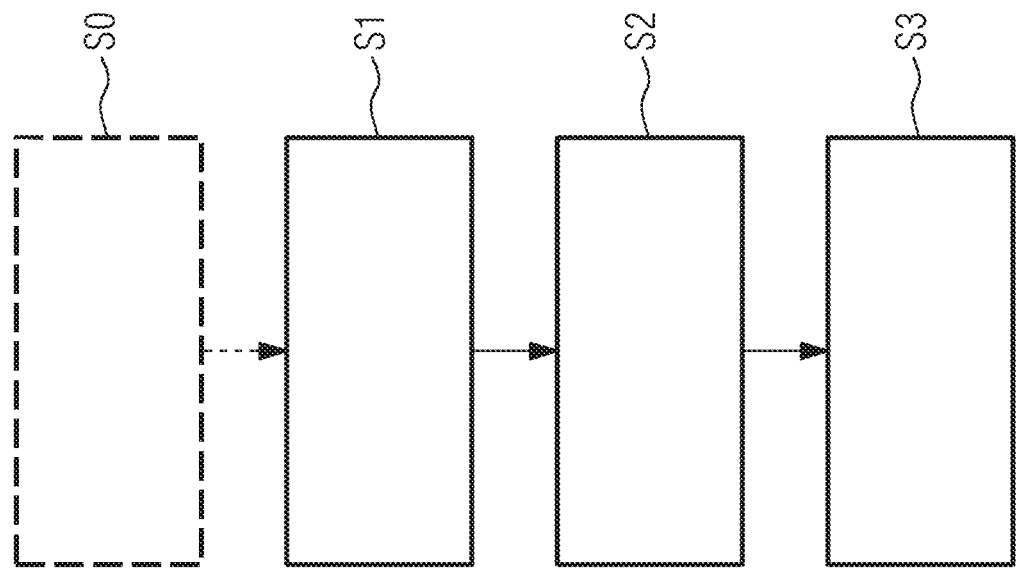
FIG. 6 shows a schematic method sequence of a method for operating an x-ray detector.

FIG. 6 shows a schematic method sequence of a method for operating an x-ray detector 2 according to an embodiment of the invention, e.g. as per one of the variants described in connection with FIGS. 1 to 4.

The method comprises the step of exposing S1 the converter unit 3 of the x-ray detector 2 to x-radiation via an x-ray source 36 and thereby generating electrical signals in the converter unit 3 which are fed into the multiplicity of pixel-electronics modules 5 of the evaluation unit 1 via the electrically conductive coupling.

The method further comprises the step of processing S2 the electrical signals that have been fed in, via a respective pixel-electronics module 5 of the multiplicity of pixel-electronics modules 5, to form a digital pixel-measurement signal.

The method further comprises the step of adapting S3, wherein at least one digital pixel-measurement signal is adapted in a pixel-electronics module 5 via the settable digital signal-processing unit 7 of the pixel-electronics module 5.

By virtue of the adaptation step S3, a correction of the pixel-measurement signal can be performed such that, based upon the adapted pixel-measurement signals, an improved data record of digital pixel-measurement signals can be provided. Based upon an improved data record, it is then possible to generate an improved x-ray image record having higher image quality. Accordingly, the method can further comprise a step of providing the digital pixel-measurement signals of the pixel-electronics modules 5, wherein at least one of the provided pixel-measurement signals is an adapted digital pixel-measurement signal.

The method can also comprise the step of adjusting so the evaluation unit 1. The adjusting S0 can include the parameterization, configuration and/or programming of at least a signal-processing unit 7 and/or an associated storage element 24, 25, 22 for at least one adaptation parameter, a configuration parameter or a program store, as a result of the signal-processing unit 7 being set by a user. In order to achieve this, the evaluation unit 1 can comprise at least one control-data input via which it is possible to transfer, select or adapt parameters or program code in order to adjust at least one signal-processing unit 7. The setting can be achieved via e.g. a computing unit 700 and an input device 47 and output device 49 coupled thereto. The user can select e.g. an adjustment, e.g. a tube current or a tube voltage of a medical apparatus, or an application routine, i.e. a specific examination type, which can then be entered into the adjustment of the evaluation unit 1. For example, an adaptation parameter set or a configuration parameter set for the signal-processing unit 7 can be automatically or semiautomatic ally selected by the computing unit 700 on this basis, and the set or alternatively just selection information transferred to the signal-processing unit 7. A selection of parameters can also take place manually, for example, by way of direct input from a user via an input unit 47 and transfer to the signal-processing unit 7.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112 (f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An evaluation circuit for an x-ray detector for signaling coupling to a converter, the converter being configured to convert incident x-radiation into electrical signals, and the evaluation circuit comprising:
   a multiplicity of pixel-electronics modules, each respective pixel-electronics module among the multiplicity of pixel-electronics modules including at least one counter or at least one integrating pixel-electronics module, the at least one counter or the at least one integrating pixel-electronics module configured to process the electrical signals to produce a corresponding processed digital pixel-measurement signal, the electrical signals being fed into the respective pixel-electronics module from the converter, each respective pixel-electronics module among the multiplicity of pixel-electronics modules including at least one corresponding settable digital signal-processor configured to adapt the corresponding processed digital pixel-measurement signal in the respective pixel-electronics module by performing at least one operation on the corresponding processed digital pixel-measurement signal, and the at least one operation being set based on at least one configuration parameter input to the at least one corresponding settable digital signal-processor.

2. The evaluation circuit of claim 1, wherein the evaluation circuit includes an application-specific integrated read-out circuit.

3. The evaluation circuit of claim 2, wherein
   the at least one corresponding settable digital signal-processor of the respective pixel-electronics module comprises a respective measurement value store, the respective measurement value store being configured to receive the corresponding processed digital pixel-measurement signal; and
   the at least one corresponding settable digital signal-processor is configured to adapt the corresponding processed digital pixel-measurement signal received by the respective measurement value store.

4. The evaluation circuit of claim 2, wherein
   the corresponding processed digital pixel-measurement signal is a corresponding current digital pixel-measurement signal; and
   the at least one corresponding settable digital signal-processor is configured to adapt the corresponding current digital pixel-measurement signal based on
      at least one corresponding previously processed digital pixel-measurement signal, or
      at least one digital pixel-measurement signal of an adjacent pixel-electronics module among the multiplicity of pixel-electronics modules.

5. The evaluation circuit of claim 2, wherein the at least one corresponding settable digital signal-processor comprises a digital circuit element including at least one of
   an adding element,
   a multiplying element,
   a dividing element,
   a calculation element for an exponential function, or
   a multiplexer.

6. The evaluation circuit of claim 2, wherein the at least one corresponding settable digital signal-processor comprises a storage element for at least one adaptation parameter or the at least one configuration parameter, the at least one adaptation parameter or the at least one configuration parameter being for adjusting the at least one corresponding settable digital signal-processor.

7. The evaluation circuit of claim 2, further comprising:
   a storage element for at least one adaptation parameter or the at least one configuration parameter, the at least one adaptation parameter or the at least one configuration parameter being for adjusting the at least one corresponding settable digital signal-processor of each respective pixel-electronics module among a plurality of the multiplicity of pixel-electronics modules.

8. The evaluation circuit of claim 2, wherein
   the at least one corresponding settable digital signal-processor comprises a processor core including an arithmetic-logic unit; and
   the at least one operation includes at least one of an arithmetic operation or a logic operation.

9. The evaluation circuit of claim 8, further comprising:
   a program store to store a program code for setting the processor core of the at least one corresponding settable digital signal-processor of a first respective pixel-electronics module among the multiplicity of pixel-electronics modules.

10. The evaluation circuit of claim 9, wherein the program store is configured for the at least one corresponding settable digital signal-processor of each respective pixel-electronics module among a plurality of the multiplicity of pixel-electronics modules.

11. An x-ray detector, comprising:
   the evaluation circuit of claim 8; and
   the converter, each respective pixel-electronics module among the multiplicity of pixel-electronics modules being coupled in an electrically conductive manner to the converter to feed the electrical signals into the respective pixel-electronics module.

12. A medical imaging device, comprising:
   at least one of the x-ray detector of claim 11; and
   an x-ray source situated opposite the at least one x-ray detector, the x-ray source being configured to expose the at least one x-ray detector to x-radiation.

13. The medical imaging device of claim 12, wherein the medical imaging device comprises a computed tomography apparatus.

14. An x-ray detector, comprising:
the evaluation circuit of claim 2; and
the converter, each respective pixel-electronics module among the multiplicity of pixel-electronics modules being coupled in an electrically conductive manner to the converter to feed the electrical signals into the respective pixel-electronics module.

15. A medical imaging device, comprising:
at least one of the x-ray detector of claim 14; and
an x-ray source situated opposite the at least one x-ray detector, the x-ray source being configured to expose the at least one x-ray detector to x-radiation.

16. The medical imaging device of claim 15, wherein the medical imaging device comprises a computed tomography apparatus.

17. The evaluation circuit of claim 1, wherein
the at least one corresponding settable digital signal-processor of the respective pixel-electronics module comprises a respective measurement value store, the respective measurement value store being configured to receive the corresponding processed digital pixel-measurement signal; and
the at least one corresponding settable digital signal-processor is configured to adapt the corresponding processed digital pixel-measurement signal received by the respective measurement value store.

18. The evaluation circuit of claim 1, wherein
the corresponding processed digital pixel-measurement signal is a corresponding current digital pixel-measurement signal; and
the at least one corresponding settable digital signal-processor is configured to adapt the corresponding current digital pixel-measurement signal based on
at least one corresponding previously processed digital pixel-measurement signal, or
at least one digital pixel-measurement signal of an adjacent pixel-electronics module among the multiplicity of pixel-electronics modules.

19. The evaluation circuit of claim 1, wherein the at least one corresponding settable digital signal-processor comprises a digital circuit element including at least one of
an adding element,
a multiplying element,
a dividing element,
a calculation element for an exponential function, or
a multiplexer.

20. The evaluation circuit of claim 1, wherein the at least one corresponding settable digital signal-processor comprises a storage element for at least one adaptation parameter or the at least one configuration parameter, the at least one adaptation parameter or the at least one configuration parameter being for adjusting the at least one corresponding settable digital signal-processor.

21. The evaluation circuit of claim 1, further comprising:
a storage element for at least one adaptation parameter or the at least one configuration parameter, the at least one adaptation parameter or the at least one configuration parameter being for adjusting the at least one corresponding settable digital signal-processor of each respective pixel-electronics module among a plurality of the multiplicity of pixel-electronics modules.

22. The evaluation circuit of claim 1, wherein
the at least one corresponding settable digital signal-processor comprises a processor core including an arithmetic-logic unit; and
the at least one operation includes at least one of an arithmetic operation or a logic operation.

23. The evaluation circuit of claim 22, further comprising:
a program store to store a program code for setting the processor core of the at least one corresponding settable digital signal-processor of a first respective pixel-electronics module among the multiplicity of pixel-electronics modules.

24. The evaluation circuit of claim 23, wherein the program store is configured for the at least one corresponding settable digital signal-processor of each respective pixel-electronics module among a plurality of the multiplicity of pixel-electronics modules.

25. An x-ray detector, comprising:
the evaluation circuit of claim 1; and
the converter, each respective pixel-electronics module among the multiplicity of pixel-electronics modules being coupled in an electrically conductive manner to the converter to feed the electrical signals into the respective pixel-electronics module.

26. A medical imaging device, comprising:
at least one of the x-ray detector of claim 25; and
an x-ray source situated opposite the at least one x-ray detector, the x-ray source being configured to expose the at least one x-ray detector to x-radiation.

27. The medical imaging device of claim 26, wherein the medical imaging device comprises a computed tomography apparatus.

28. A method for operating an x-ray detector, comprising:
exposing a converter of the x-ray detector to x-radiation via an x-ray source to generate electrical signals in the converter, the electrical signals being fed into a multiplicity of pixel-electronics modules of an evaluation circuit of the x-ray detector via an electrically conductive coupling;
processing the electrical signals via respective pixel-electronics modules among the multiplicity of pixel-electronics modules to form corresponding digital pixel-measurement signals, the processing being performed via at least one counter of the respective pixel-electronics module or at least one integrating pixel-electronics module of the respective pixel-electronics module; and
adapting at least one corresponding digital pixel-measurement signal among the corresponding digital pixel-measurement signals in a respective pixel-electronics module among the respective pixel-electronics modules, the adapting being performed via a settable digital signal-processor of the respective pixel-electronics module, the adapting including performing at least one operation on the at least one corresponding digital pixel-measurement signal, and the at least one operation being set based on at least one configuration parameter input to the settable digital signal-processor.

* * * * *